United States Patent
Dubrul et al.

(10) Patent No.: US 6,530,923 B1
(45) Date of Patent: Mar. 11, 2003

(54) TISSUE REMOVAL METHODS AND APPARATUS

(75) Inventors: William R. Dubrul, Redwood City, CA (US); Richard E. Fulton, Grand Junction, CO (US); Robert M. Curtis, Hillsborough, CA (US)

(73) Assignee: Artemis Medical, Inc., Hayward, CA (US)

( * ) Notice: Subject to any disclaimer, the term of this patent is extended or adjusted under 35 U.S.C. 154(b) by 148 days.

(21) Appl. No.: 09/588,278

(22) Filed: Jun. 5, 2000

Related U.S. Application Data

(63) Continuation-in-part of application No. 09/336,360, filed on Jun. 18, 1999, now Pat. No. 6,270,464, which is a continuation-in-part of application No. 09/248,088, filed on Feb. 9, 1999, now Pat. No. 6,221,006.
(60) Provisional application No. 60/137,775, filed on Jun. 4, 1999, provisional application No. 60/146,892, filed on Aug. 2, 1999, provisional application No. 60/200,546, filed on Apr. 27, 2000, provisional application No. 60/154,394, filed on Sep. 17, 1999, provisional application No. 60/090,243, filed on Jun. 22, 1998, provisional application No. 60/092,734, filed on Jul. 14, 1998, provisional application No. 60/114,863, filed on Jan. 6, 1999, provisional application No. 60/117,421, filed on Jan. 25, 1999, provisional application No. 60/074,199, filed on Feb. 10, 1998, and provisional application No. 60/105,284, filed on Oct. 22, 1998.

(51) Int. Cl.$^7$ .................................................. A61B 17/17
(52) U.S. Cl. ..................... 606/45; 606/113; 606/114; 128/898
(58) Field of Search ...................... 128/898; 606/158, 606/159, 160, 113, 114, 115, 127, 128, 200, 45, 46

(56) References Cited

U.S. PATENT DOCUMENTS 3,996,938 A   12/1976   Clark, III ................ 128/348

(List continued on next page.)

FOREIGN PATENT DOCUMENTS

| DE | 39 13935 | 4/1989 |
|---|---|---|
| EP | 966 920 | 12/1999 |
| EP | 983 749 | 3/2000 |
| GB | 2020557 | 11/1979 |
| WO | WO 95/20370 | 1/1995 |
| WO | WO 00/12009 | 3/2000 |
| WO | WO 00/12010 | 3/2000 |
| WO | WO 02/05717 A1 | 1/2002 |

Primary Examiner—Rosilang S. Kearney
(74) Attorney, Agent, or Firm—James F. Hann; Haynes Beffel & Wolfeld LLP

(57) ABSTRACT

Target tissues are accessed and removed using various types of devices and methods.

6 Claims, 7 Drawing Sheets

U.S. PATENT DOCUMENTS

| | | |
|---|---|---|
| 4,425,908 A | 1/1984 | Simon |
| 4,608,965 A | 9/1986 | Anspach, Jr. et al. |
| 4,611,594 A | 9/1986 | Grayhack et al. ............ 128/328 |
| 4,638,802 A | 1/1987 | Okada |
| 4,650,466 A | 3/1987 | Luther .......................... 604/95 |
| 4,799,495 A | 1/1989 | Hawkins et al. ............. 128/754 |
| 4,907,589 A | 3/1990 | Cosman |
| 5,030,201 A | 7/1991 | Palestrant .................... 604/22 |
| 5,100,423 A | 3/1992 | Fearnot |
| 5,102,415 A | 4/1992 | Guenther et al. ............ 606/159 |
| 5,183,463 A | 2/1993 | Debbas ......................... 604/98 |
| 5,183,464 A | 2/1993 | Dubrul et al. .................. 128/3 |
| 5,221,269 A | 6/1993 | Miller et al. ................. 604/281 |
| 5,330,483 A | 7/1994 | Heaven et al. |
| 5,415,656 A | 5/1995 | Tihon et al. |
| 5,431,676 A | 7/1995 | Dubrul et al. ............... 606/185 |
| 5,454,790 A | 10/1995 | Dubrul ....................... 604/104 |
| 5,634,883 A | 6/1997 | Chin et al. |
| 5,643,282 A | 7/1997 | Kieturakis .................. 606/114 |
| 5,735,289 A | 4/1998 | Pfeffer et al. |
| 5,792,157 A | 8/1998 | Mische et al. ............... 606/159 |
| 5,794,626 A | 8/1998 | Kieturakis |
| 5,795,308 A | 8/1998 | Russin ........................ 600/567 |
| 5,803,901 A | 9/1998 | Chin et al. |
| 5,807,276 A | 9/1998 | Russin ........................ 600/567 |
| 5,827,324 A | 10/1998 | Cassell et al. ............... 606/200 |
| 5,868,708 A | 2/1999 | Hart et al. ................... 604/104 |
| 5,928,260 A | 7/1999 | Chin et al. ................... 606/200 |
| 6,027,520 A | 2/2000 | Tsugita et al. ............... 606/200 |
| 6,053,876 A | 4/2000 | Fisher |
| 6,136,014 A | 10/2000 | Sirimanne et al. |
| 6,161,034 A | 12/2000 | Burbank et al. |
| 6,261,241 B1 | 7/2001 | Burbank et al. |
| 6,277,083 B1 | 8/2001 | Eggers et al. |
| 6,312,429 B1 | 11/2001 | Burbank et al. |
| 6,331,166 B1 * | 12/2001 | Burbank |
| 2002/0007130 A1 | 1/2002 | Burbank et al. |
| 2002/0016555 A1 | 2/2002 | Ritchart et al. |
| 2002/0019640 A1 | 2/2002 | McGuckin, Jr. |
| 2002/0026201 A1 | 2/2002 | Foerster et al. |

\* cited by examiner

TISSUE REMOVAL METHODS AND APPARATUS

CROSS-REFERENCES TO RELATED APPLICATIONS

This application claims the benefit of the following provisional patent applications: Provisional Application No. 60/137,775 filed Jun. 4, 1999 and entitled TISSUE REMOVAL APPARATUS AND METHOD FOR USE; Provisional Application No. 60/146,892 filed Aug. 2, 1999 entitled DISEASE PREVENTING SHEATH APPARATUS AND METHODS FOR USE; Provisional Application No. 60/200,546 filed Apr. 27, 2000 and entitled DIAGNOSTIC AND THERAPEUTIC APPARATUSES AND METHODS FOR USE; Provisional Application No. 60/154,394 filed Sep. 17, 1999 and entitled ONCOLOGICAL APPARATUS AND METHOD FOR USE. This application is also a continuation-in-part of U.S. patent application Ser. No. 09/336,360 filed Jun. 18, 1999 entitled BIOPSY LOCALIZATION METHOD AND DEVICE; U.S. Pat. No. 6,270,464 which application claims priority from the following provisional applications:

Application No. 60/090,243, filed Jun. 22, 1998;
  Application No. 60/092,734, filed Jul. 14, 1998;
  Application No. 60/114,863, filed Jan. 6, 1999; and
  Application No. 60/117,421, filed Jan. 25, 1999.

This application is also a continuation-in-part of U.S. patent application Ser. No. 09/248,088 filed Feb. 9, 1999, U.S. Pat. No. 6,221,006 which application claims benefit of the following provisional applications:

Application No. 60/074,199 filed Feb. 10, 1998; and
  Application No. 60/105,284 filed Oct. 22, 1998.

BACKGROUND OF THE INVENTION

The M. D. Anderson Cancer Center in Houston, Texas predicts that cancer will become the leading cause of death in the United States by the year 2002. Cancer presently results in over one thousand five hundred deaths every day in the United States (550,000 deaths every year). Therapy modalities for cancer are plentiful and continued to be researched with vigor. Still, the preferred treatment continues to be physical removal of the cancer. When applicable, surgical removal is preferred (breast, colon, brain, lung, kidney, etc.). Open, excisional, surgical removal is often extremely invasive so that efforts to remove cancerous tissue in less invasive ways continue, but have not yet been perfected.

The only cure for cancer continues to be the early diagnosis and subsequent early treatment. As cancer therapies continue at earlier stages of diagnosis, the cancerous tissue being operated on is also smaller. Early removal of the smaller cancers demand new techniques for removal and obliteration of these less invasive cancers.

There are a variety of techniques that attempt to accomplish less invasive cancer therapy, but so far without sufficiently improved results. For example, the ABBI system from U.S. Surgical Corporation and the Site Select system from Imagine Corporation, attempt to accomplish less invasive cancer therapy. However, conventional techniques require more than Minimally Invasive Surgery (MIS) techniques in that they require a large core (that is more than about 15 mm diameter) incision. Additionally, the Mammotome system from Johnson and Johnson and MIBB system from U.S. Surgical Corporation also require large core (over about 4 mm diameter) access to accomplish biopsy.

A recent convention held by the American Society of Surgical Oncologists on Mar. 13, 2000 reported that conventional stereotactic core biopsy (SCB) procedures fall short in providing definitive answers to detail precise surgical regimens after this SCB type vacuum assisted biopsy, especially with ductile carcinoma in situ (DCIS). Apparently these percutaneous systems damage "normal" tissue cells so that it is difficult to determine if the cells are "normal damaged" cells or early pre-cancerous (e.g. Atypical Ductal Hyerplasi (ADH)) cells.

A study presented by Dr. Ollila et al. from the University of North Carolina, Chapel Hill, demonstrated that histology and pathology is compromised using these conventional techniques because of the damage done to the removed tissue specimens. Hence, for many reasons, including the fact that DCIS is becoming more detectable and hence more prevalent in breast cancer diagnosis in the U.S., there is a growing need to improve upon conventional vacuum assisted core biopsy systems.

SUMMARY OF THE INVENTION

Broadly, the present invention is directed to procedures, including biopsy and tumorectomy methods, and associated apparatus which provide for less invasive techniques while also providing for enhanced tissue specimens being retrieved.

A first aspect of the invention is directed to a tissue removal method in which a tissue separation device is positioned at a target site within a patient. A tissue sample is separated by the movement of tissue separation element through the tissue at the target site. A factor relating to the restriction of the passage of the tissue separation element through the tissue is monitored so that energy supplied to the tissue separation element can be adjusted. The procedure may be carried out percutaneously. The method may include radially expanding one or more heated, wire-type tissue separation elements and then rotating the support shaft. The factor being monitored may include, for example, strain on the tissue separation element, the rotational force supplied to the device, the pressure exerted against the tissue by the tissue separation element, etc. Monitoring may also be done manually with tactile feedback to the user.

A related aspect of the invention is directed to a tissue removal assembly in which an elongate tissue separation device comprises a tissue separation element mounted to a support. The tissue separation element is movable from a retracted state to an extended state. A tissue separation element driver is operably coupled to the tissue separation element to permit the tissue separation element to separate a target tissue mass from a patient. The tissue separation element driver comprises an energy source coupled to the tissue separation device. A sensor is operably coupled to at least one of the tissue separation device and the tissue separation element driver and senses resistance to the separation of the target tissue mass from the patient. A feedback device operably couples the sensor and the tissue separation element driver so that the amount of energy supplied can be adjusted based on the resistance to the passage of the tissue separation element through the patient's tissue.

Certain advantages accrue through the use of the above-described tissue removal method and assembly. An appropriate amount of energy can be supplied to the tissue separation element so that when, for example, the tissue separation element is a wire which extends radially outwardly to form an arch passing through the target tissue, the wire can be heated so to cauterize the tissue it passes through as it moves from the radically retracted state to the radically extended state; this helps to prevent spreading of viable cancer tissue into non-cancerous tissue regions. Heating or otherwise energizing the tissue separation element with RF energy, vibrational or other mechanical energy, etc., may also reduce the force required to move the tissue separation element through tissue mass, especially when passing through dense or fibrotic tissue or a variation in densities. Once the tissue separation element has been fully extended, it may or may not need to be heated or otherwise energized to pass through non-diseased tissue surrounding the suspect tissue mass. Therefore, undesirable damage to healthy tissue may be minimized and the spread of cancerous tissue to non-cancerous tissue may be effectively eliminated.

A further aspect of the invention is directed to a method for helping to prevent seeding of a tissue tract including positioning a protective device along the tissue tract and then moving tissue from the target site, through an opening in the protective device and into an inner region of the protective device. The tissue is then moved along the tissue tract and out of the patient while keeping the tissue within the device. The protective device may be maintained substantially in place along the tissue tract as the tissue is moved out of the patient.

Another aspect of the invention is directed to percutaneous tissue mass retrieval assembly comprising a shaft, a radially expandable blocking element at the distal end of the shaft, a suspect tissue mass enveloping device movable from an enlarged, tissue mass-surrounding state to a contracted, tissue mass-constricting state so to enable the tissue mass to be removed from a target site with a reduced lateral size.

A still further aspect of the invention is directed to a method for maintaining access to a void within a patient by placing an access sleeve along a tissue tract connecting an access site in the patient's skin and a void in the patient. This method may take place, for example, following the removal of a biopsy specimen, the removal creating the void. The method may also take place following removal of an entire suspect tissue mass as well. This method ensures convenient and accurate re-access to the void when, for example, an additional tissue sample is needed, therapeutic drugs are to be delivered to the void, a prosthesis is to be implanted, etc.

An additional aspect of the invention is directed to a method for removal of target material from a target site and includes percutaneously placing an expandable blocking element at a first position distal of the target material, expanding the expandable blocking element, percutaneously placing a removing element at a second position, at least substantially surrounding the target material with the blocking element and the removing element, and then removing the blocking element, the removing element and the target material therewith from the patient along a tissue tract connecting the target site with an access site in the patient's skin. The expandable blocking element may be a radially expandable, tubular mesh material. The removing element may include a tubular mesh element having a radially expandable, open distal end. One or both of the removing element and blocking element may be at least partially radially collapsed prior to removing the blocking element, removing element and target material therewith from the patient. This method helps to ensure target material is properly captured and permits it to be removed percutaneously; the removal may be preceded by radially collapsing the blocking and/or removing elements to help reduce the size of the device passing through the access site in the patient's skin.

A still further aspect of the invention relates to a target material removing device including a shaft, first and second axially spaced-apart, radially expandable elements carried by a distal portion of the shaft. The expandable elements are remotely selectively movable between radially retracted and radially expanded states so that the expandable elements can be used to bracket target material to permit the target material to be removed from the patient along with the device. This device permits a surgeon to easily and accurately locate the target material, which is often very difficult to visually differentiate from surrounding tissue, by locating the expandable elements. The radially expandable elements are preferably sufficiently hard so as to be detectable by palpation.

A still another aspect to the invention is directed to a method for locating a target mass within a patient comprising extending the distal end of a shaft to a position distal of a target mass, positioning first and second radially expanding bracketing elements at positions distal of and proximal of the target mass, moving the bracketing elements from radially retracted states to radially expanded states thereby bracketing the target mass, and locating a target mass using the bracketing elements. The bracketing elements, when radially expanded, may define a bracketed region therebetween sized to completely contain the target mass. The target mass may be located by palpation of the bracketing elements or with the aid of a surgical incision at least partially exposing at least one of the bracketing elements.

An additional aspect to the invention is directed to a method for maintaining percutaneous access to an excisional site comprising positioning first and second locational elements within a patient at a target site, the locational elements carried by elongate elements extending from the locational elements along a tissue tract and out through an access site in the patient's skin. The first elongate element and first locational element therewith are then removed from the patient and the target site is accessed using the second elongate element and second locational element therewith. The second or both the first and second locational elements may be radially expandable locational elements. This aspect of the invention provides the surgeon the ability to accurately locate the target site. It also permits one of the locational elements to be removed and one to be left at the target site.

A still additional aspect of the invention is directed to a percutaneous access assembly including first and second separately movable locational devices, each device including a shaft and a radially expandable element mounted to the shaft. The radially expandable elements are locatable adjacent to one another.

Other features and advantages of the invention will appear from the following description in which the preferred embodiments and methods have been set forth in detail in conjunction with the accompanying drawings.

DESCRIPTION OF THE SPECIFIC EMBODIMENTS

Figure 1A:
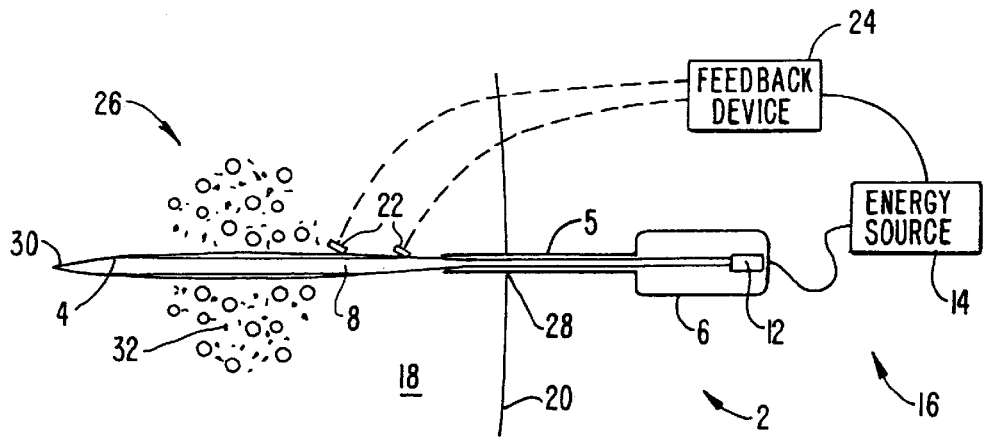
FIGS. 1A–1C illustrate the use of a tissue removal assembly made according to the invention.
Figure 1B:
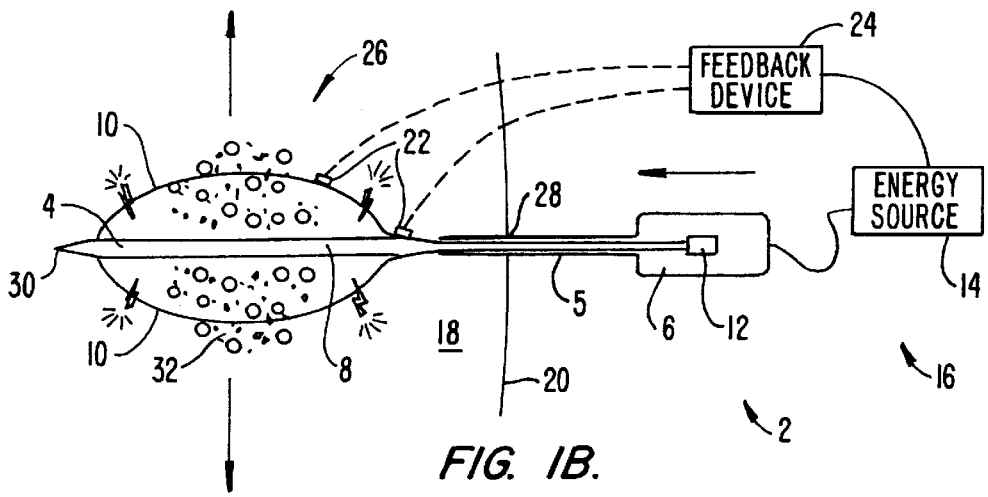
Figure 1C:
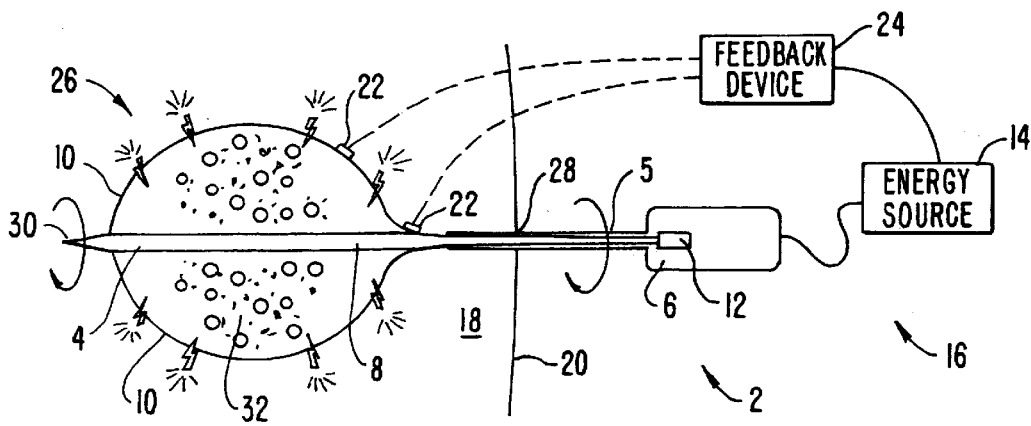

FIGS. 1A–1C illustrate the use of a tissue removal assembly 2. Tissue removal assembly 2 includes a support shaft 4 passing through an introducer sheath 5 extending from a handle 6. The distal portion 8 of shaft 4 has a pair of tissue separation wires 10 mounted thereto. Wires 10 are movable from a retracted state of FIG. 1A to a fully extended state of FIG. 1C by moving a slide 12 mounted to handle 6 as indicated in FIGS. 1A–1C. Wires 10 are typically made of tungsten or stainless steel and may have a round, rectangular or other cross-sectional shape depending upon the type of tissue and other matter expected to be encountered. U.S. patent application Ser. No. 09/248,088 and Provisional Applications 60/154,394 (filed Sep. 17, 1999 and entitled Oncological Apparatus and Method for Use) and No. 60/200,546 describe various tissue separation elements. Wires 10 are coupled to an energy source 14 to supply wires 10 with appropriate energy to aid the cutting or other separating actions of the wires, including electrical, RF, vibrational, electromagnetic, etc. Together, handle 6 and energy source 14 constitute a wire tissue separation element driver 16 because both act to help move wires 10 through tissue 18 beneath a skin surface 20 of the patient.

Appropriate sensors 22 are mounted to one or more of wires 10 and shaft 4. Sensors 22 may include strain gauge sensors, pressure sensors, temperature sensors, etc. Sensors 22 are coupled to a feedback device 24 through sheath 5; feedback device 24 is connected to energy source 14 to ensure that energy source 14 provides an appropriate level of energy to wires 10.

Assembly 2 is used to percutaneously access a target site 26 through an access site 28 in skin surface 20 while in the retracted state. The tip 30 of shaft 4 is positioned distally of the target tissue mass 32. In some situations it may be desirable to pass tip 30 directly through target tissue mass 32 while in other situations it may be desirable to have shaft 4 pass to one side of target tissue mass 32. Once properly positioned, which is preferably accomplished with the aid of remote visualization techniques, such as x-rays, ultrasound, etc., slide 12 is moved in a distal direction causing wires 10 to arc outwardly from the retracted state of FIG. 1A, through the intermediate extended state of FIG. 1B and to the fully extended state of FIG. 1C. Wires 10 are preferably energized, typically by heating using resistance or RF heating techniques, as wires 10 pass through tissue 18. This is very important when wires 10 pass through target tissue mass 32 and the target tissue mass contains, or possibly contains, cancerous or other diseased tissue. By appropriately energizing wires 10, the tissue wires 10 pass through is, for example, cauterized so that no viable diseased tissue is pulled along with the radially outwardly expanding wires; this helps to keep the healthy tissue surrounding target tissue mass 32 free from viable diseased tissue. In addition to heating the tissue, tissue removal assembly 2 may be provided with vibrational, reciprocating or other mechanical energy to help passage of wires 10 through tissue 18.

Once fully expanded, tissue removal assembly 2 is rotated, typically by the user manually grasping and rotating handle 6. If the desired, a motorized or other non-manual rotation of assembly 2 could be provided for. Sensors 22 provide appropriate information to feedback device 24 so to ensure a proper amount of energy is supplied to wires 10 to, among other things, ensure proper cauterization of the tissue as wires 10 are moved readily outwardly while not overly damaging the tissue. Once in the fully extended state of FIG. 1C, the amount of energy supplied to wires 10 may not need to be as great as when, for example, wires 10 pass through only healthy tissue. Therefore, if wires 10 cease to be driven and thus stop moving through the tissue, feedback can result in a halt in the supply of energy to wires 10.

In the embodiment of FIGS. 1A–1C two wires 10 are used. This causes target tissue mass 32 to be cut away from the surrounding tissue in two contiguous tissue masses. If desired, only a single wire 10 or more than two wires 10 could be used. Using the method described with respect to FIGS. 1A–1C, the entire target tissue mass 32 may be removed in a simultaneous manner. This aspect of the invention will be described in more detail below with reference to FIGS. 4A–4D. All or part of the procedure, such as expanding, cutting, rotating, energizing, etc., could be automated.

Additional aspects of the invention will be described below with reference to additional figures, with like structure referred to with like reference numerals.

Figure 2:
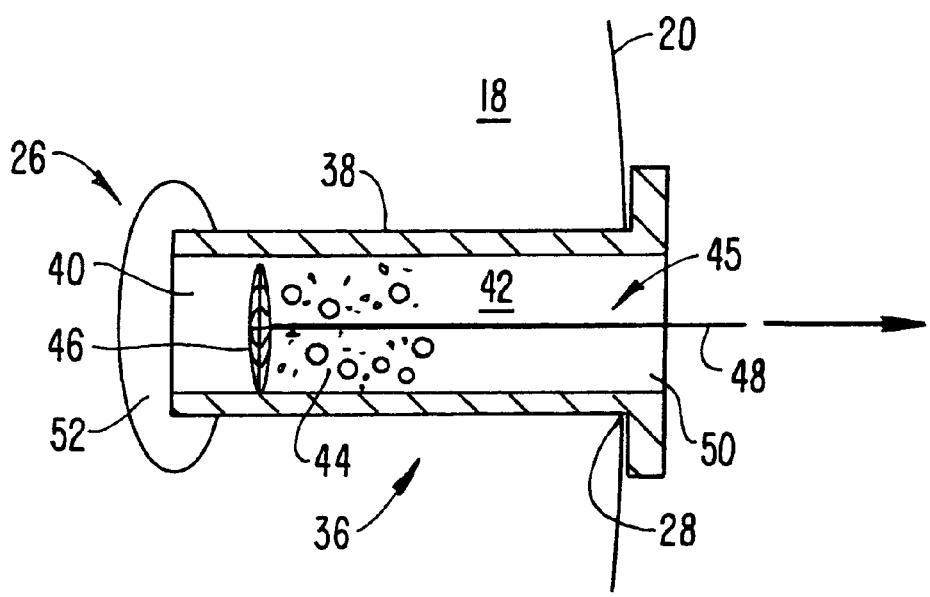
FIG. 2 shows the use of a sleeve which helps prevent seeding of a tissue tract and provides access to a void within the patient.

FIG. 2 illustrates two additional aspects of the invention. A sleeve 36 is used to help prevent seeding of a tissue tract 38 extending between access site 28 and target site 26. Protective sleeve 36 is positioned along tissue tract 38 and has a distal opening 40, preferably positioned adjacent to or within target site 26, and an open interior 42. Target tissue 44 is moved from target site 26 through opening 40 and into open interior 42. FIG. 2 illustrates this having been accomplished using a tissue engagement device 45 having a radially expandable mesh device 46 at the distal end of a shaft 48. Mesh device 46 is of a type which can be movable from a generally cylindrical orientation, not shown, to the radially extended configuration shown in FIG. 2 by pushing the distal ends of the cylindrical mesh material towards one another. Examples of this type of mesh structure can be found in U.S. patent application Ser. No. 09/376,678 filed Aug. 18, 1999, entitled Target Tissue Localization Device and Method and in Provisional Application No. 60/200,546. Other methods and devices for moving target tissue 44 from target site 26 into interior 42 can also be used. Target tissue 44 can then be removed from the patient by either leaving protective sleeve 36 in place and sliding the target tissue out through the opened proximal end 50 of sleeve 36 or by removing the entire structure, that is protective sleeve 36, mesh device 46, shaft 48 and target tissue 44 therewith, from tissue track 38 of the patient.

A further aspect of the invention can also be discussed with reference to FIG. 2. In this aspect of the invention, access to a void 52 within a patient can be maintained by placing sleeve 36 along tissue tract 38 and leaving it in place. This method may be accomplished after removal of, for example, a biopsy specimen or an entire suspect tissue mass. This provides convenient and accurate re-access to void 52. Such re-access may be used, for example, when additional tissue samples are needed, therapeutic drugs need to be delivered to void 52, a prosthesis is to be implanted into void 52, or for other reasons.

Figure 3A:
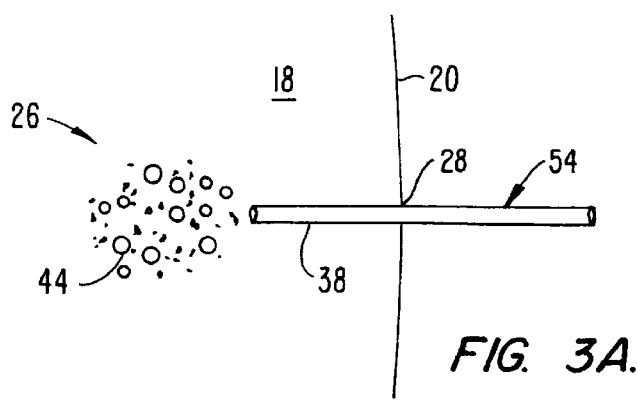
FIGS. 3A–3H illustrate a further aspect of the invention by which percutaneous removal of target tissue from a target site within the patient is accomplished using a radially expandable/collapsible tubular shaft.
Figure 3B:
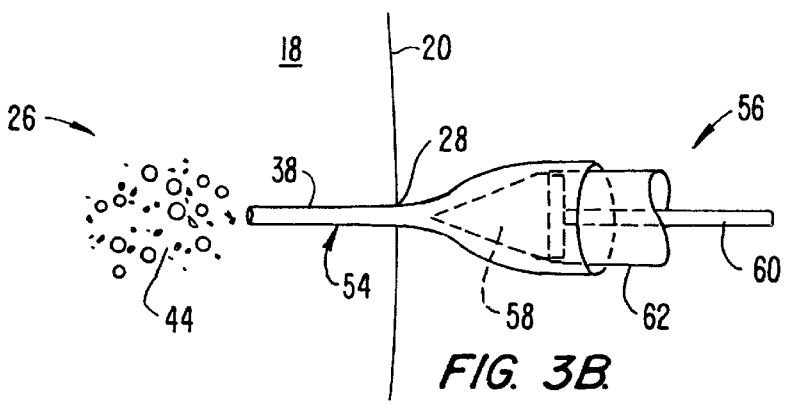
Figure 3C:
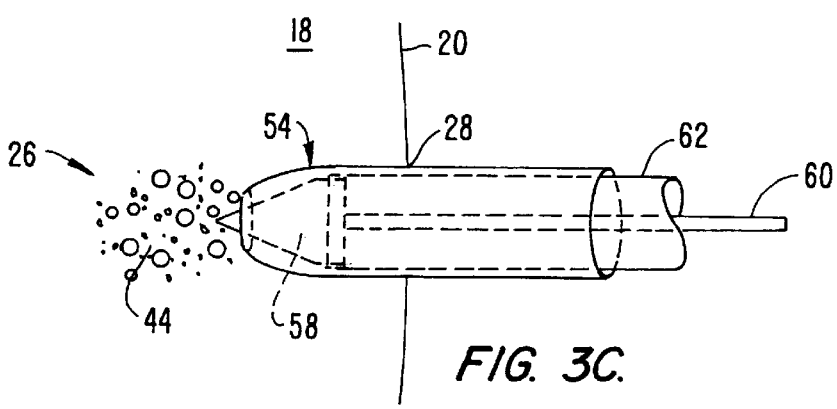
Figure 3D:
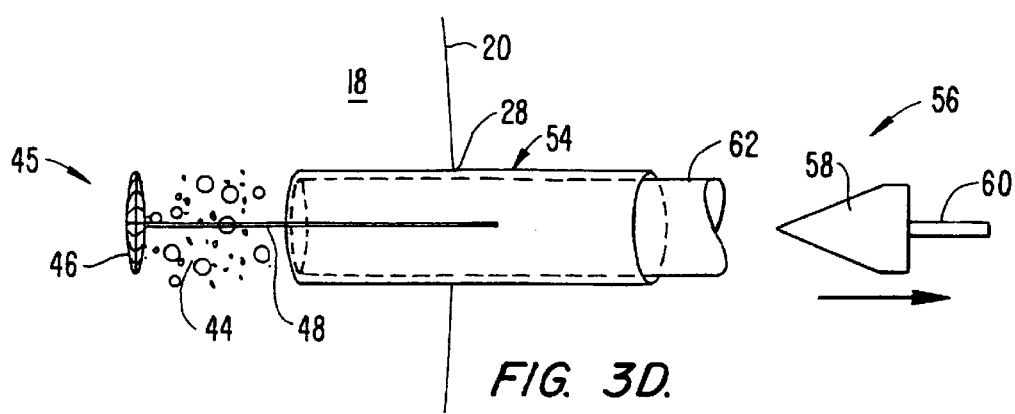
Figure 3E:
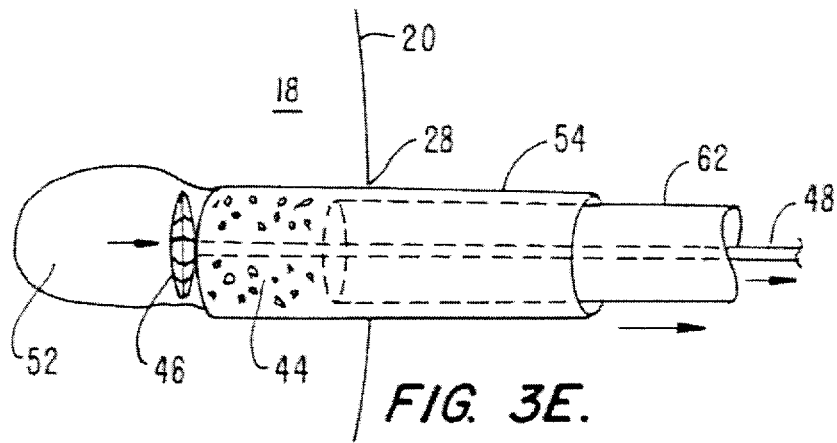

FIGS. 3A–3H illustrate another aspect of the invention by which percutaneous removal of target tissue 44 from target site 26 is accomplished. A hollow, radially expandable/collapsible tubular shaft 54 is passed along tissue tract 38 when in a radially collapsed condition as shown in FIG. 3A. FIG. 3B illustrates the introduction of a tubular enlarger 56 including a conical tip 58 mounted to the distal end of a shaft 60 and a stabilizing sleeve 62 extending proximally from conical tip 58. As illustrated in FIGS. 3B and 3C, pushing enlarger 56 through shaft 54 causes the shaft to radially enlarge along its length; stabilizing sleeve 62 resists the tendency of shaft 54 to radially collapse. Once sleeve 62 is properly positioned within shaft 54, shaft 60 and tip 58 therewith are removed from within sleeve 62 as shown in FIG. 3D. Also, FIG. 3D illustrates the positioning of a tissue engagement device 45 to help draw a sample of target tissue 44 into the interior 64 of sleeve 62 as suggested in FIGS. 3D and 3E.

Figure 3F:
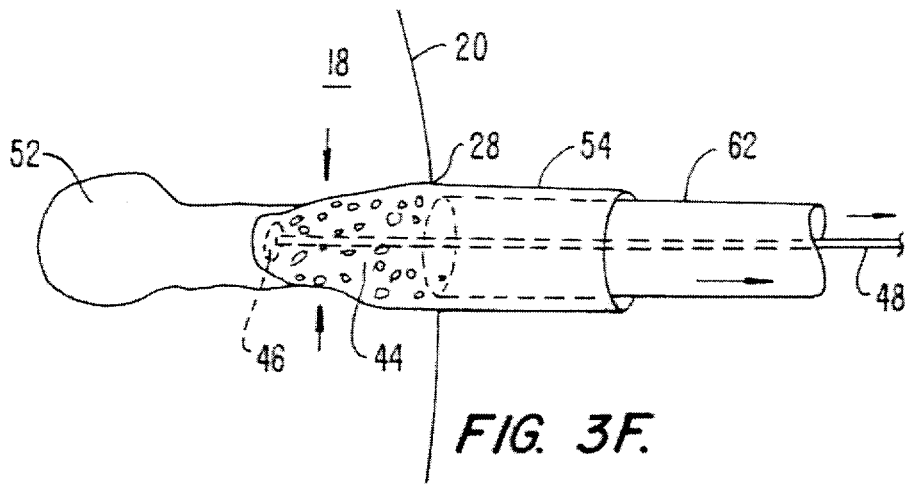
Figure 3G:
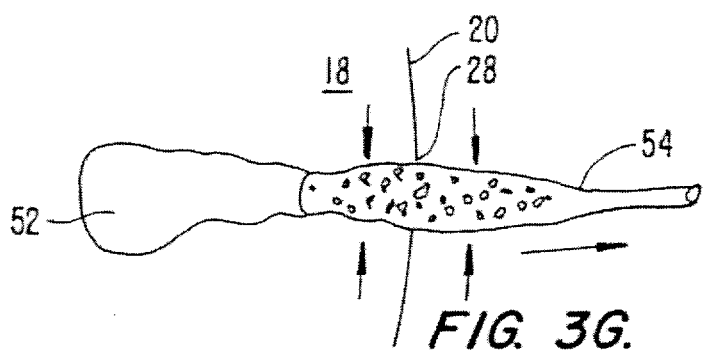
Figure 3H:
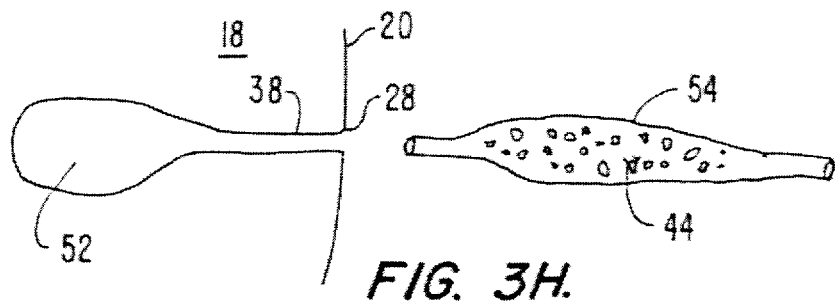

At this point a sample of the target tissue 44 may be removed from the patient by simultaneously removing shaft 54 in its enlarge diameter form, sleeve 62 and device 45 as a unit. Alternatively, stabilizing sleeve 62 may be removed as device 45 pulls tissue 44 into shaft 54 while shaft 54 remains in place. This suggested in FIGS. 3E and 3F and permits shaft 54 to return towards its initial, radially contracted condition thus causing the tissue sample housed therein to be radially compressed. The collected target tissue 44 remains within shaft 54 when sleeve 62 is removed from shaft 54 and mesh device 46 is collapsed (see FIG. 3F). Shaft 54 then naturally assumes a smaller diameter condition as shown in FIGS. 3F and 3G which permits shaft 54 and the target tissue therein to be removed through access site 28 as shown in FIGS. 3G and 3H. In this way the size of access site 28 may be smaller than the original size of target tissue 44. Device 45 may remain within shaft 54 during this removal from the patient, or device 45 may, as suggested in FIGS. 3G and 3H, be removed from shaft 54 along with sleeve 62.

The entire shaft 54 was enlarged in the embodiment of FIGS. 3A–3H. If desired, only the part of shaft 54 within the patient may need to be expanded. This would reduce the maximum size which access site 28 is forced to assume, even if only temporarily. The following U.S. Patents show radially-expanding dilators: U.S. Pat. Nos. 5,183,464; 5,431,676; 5,454,790.

Figure 4A:
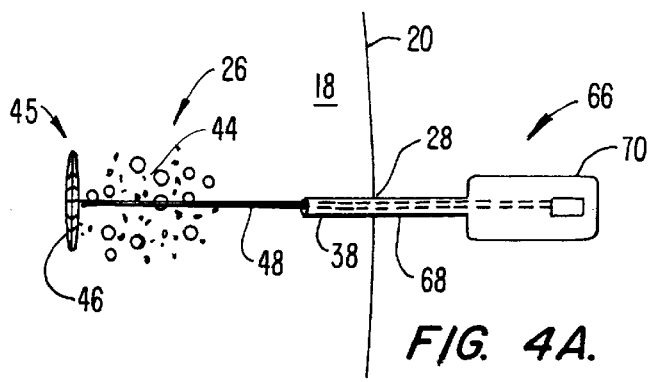
FIGS. 4A–4D show a method for percutaneously removing an entire tissue mass from a target site.
Figure 4B:
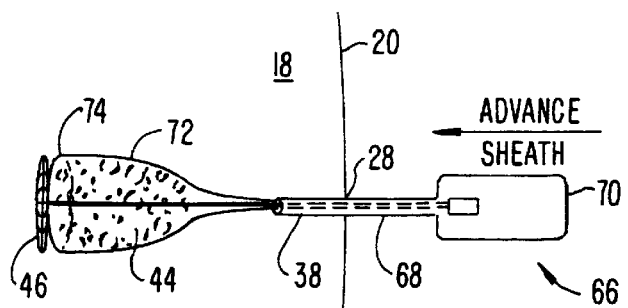
Figure 4C:
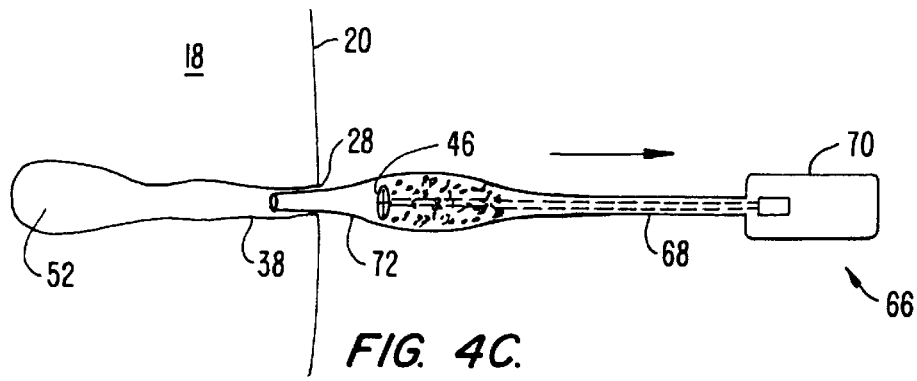
Figure 4D:
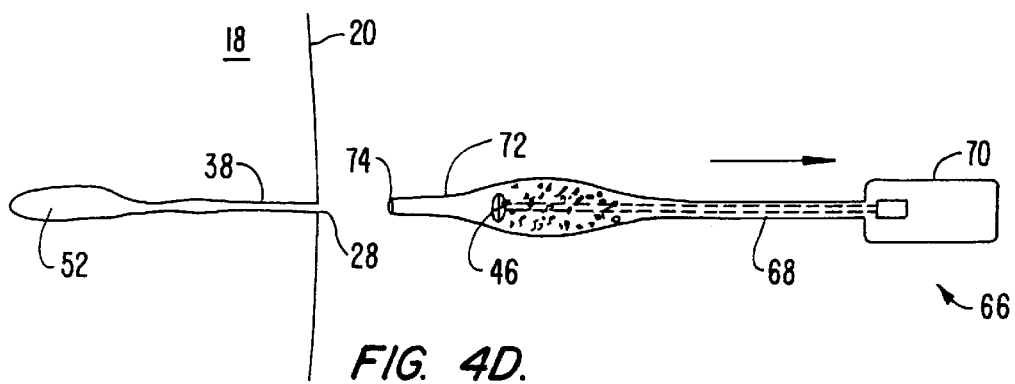

FIGS. 4A–4D illustrate a method for percutaneously removing an entire tissue mass containing target tissue 44. A tissue removal assembly 66 includes a sheath 68 extending from a proximal end adapter 70 and passes through an access site 28 and along tissue tract 38. Sheath 68 houses a tissue engagement device 45, shown in FIG. 4A, after having passed by or through target tissue 44 and manipulated to cause mesh device 46 to assume a radially expanded condition. Next, a tubular mesh device 72 is used to surround target tissue 44. Device 72 is of the type in which a tubular mesh material having an open distal end expands radially outwardly as it is compressed axially. That is, the resistance to the axial movement mesh device 72 causes it to contract axially and expand radially to assume the generally funnel-shaped configuration of FIG. 4B. As shown in FIG. 4B, mesh device 46 acts as a blocking element and mesh device 72 acts as a removing element. Together devices 46, 72 at least substantially surround, and preferably fully surround or envelope, target tissue 44.

The entire suspect tissue mass, that is the mass including target tissue 44 and an amount of surrounding tissue, can be removed through access site 28. To help prevent trauma to access site 28 during such removal, mesh device 46 and tubular mesh device 72 are caused to contract radially, thus compressing target tissue 44 into a smaller diameter mass for ease of removal from the patient. This is suggested in FIGS. 4C and 4D. The construction and use of structure similar to device 72 is described in patent application Ser. No. 09/248,008 and Provisional Application No. 60/200,546. Note that the structure shown in FIGS. 1A–1C could be used to severe target tissue 44 so that the entire suspect tissue mass, that is including target tissue 44, may be simultaneously removed as two contiguous pieces from the patient along the tissue tract. It is expected that the entire suspect tissue mass could be severed into at most four contiguous pieces and still be simultaneously removed in a useful condition for further testing and/or evaluation. One such structure could use the cutting device of FIGS. 1A–1C plus a mesh material similar to tubular mesh device 72 which could be guided by expanded wires 10 to surround the suspect tissue mass. As seen by comparing FIGS. 4B and 4C, the largest lateral dimension of the access opening 28 is smaller than the largest lateral dimension of a suspect tissue mass prior to removal; radially or laterally squeezing the suspect tissue mass permits removal of the tissue mass with minimal trauma to the patient. The suspect tissue mass may be monitored for disease prior to, during and/or after removal from the patient.

Figure 5A:
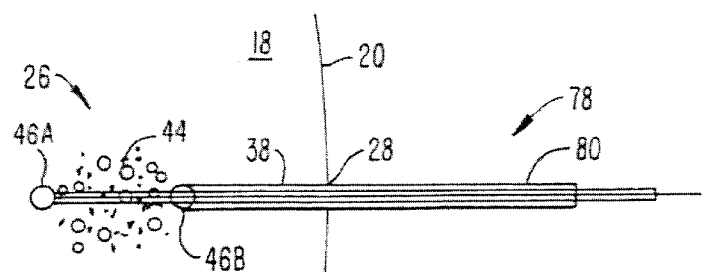
FIGS. 5A–5D illustrate a target tissue removing device including a pair of tissue engaging devices which bracket the target tissue.
Figure 5B:
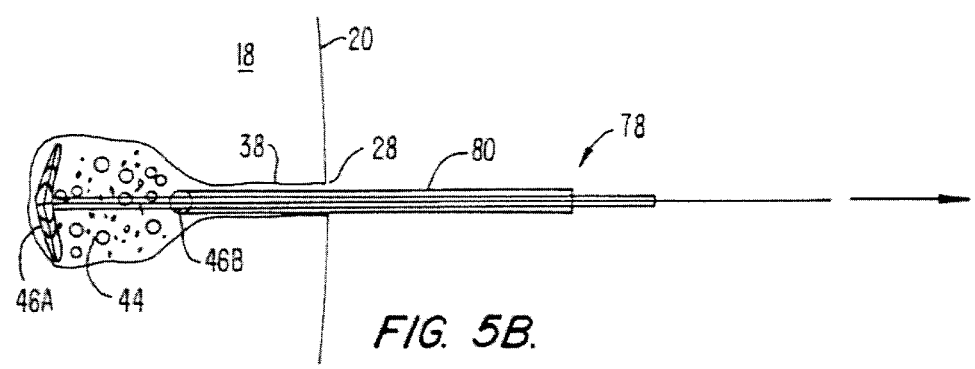
Figure 5C:
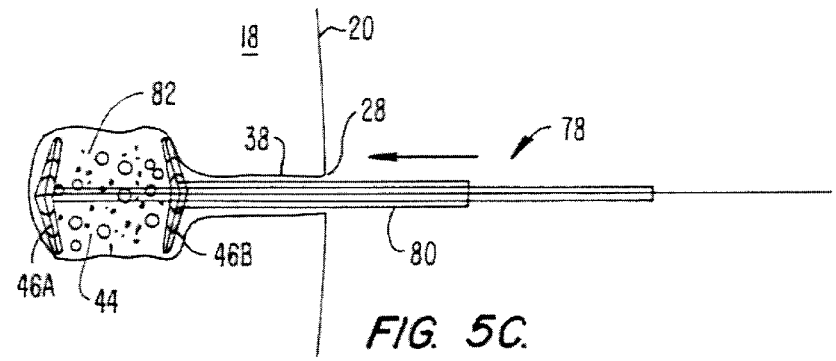
Figure 5D:
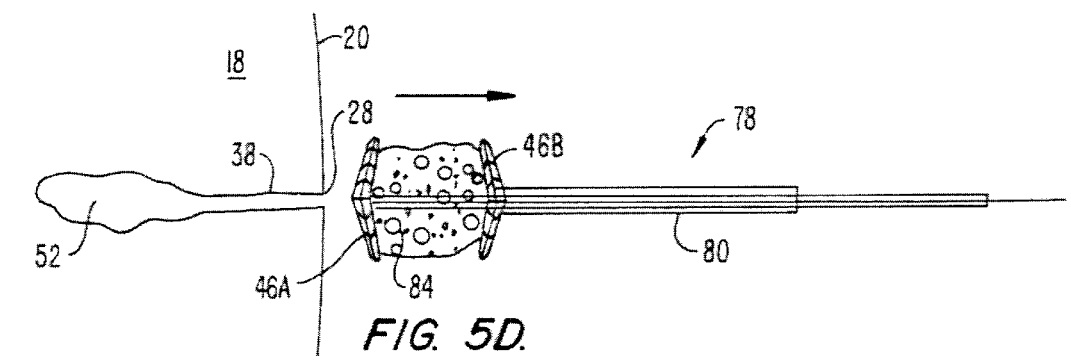

FIGS. 5A–5D illustrate a target material removing device 78 including a sheath 80 within which a pair of tissue engaging devices 45 slidable pass. FIG. 5A illustrates device 78 passing through access site 28, along tissue tract 38 and to target tissue 44 at target site 26. The first and second mesh devices 46A, 46B are placed at distal and proximal locations relative to target tissue 44. Once in position, mesh devices 46 are expanded as shown in FIGS. 5B and 5C so to bracket target tissue 44. Mesh devices 46A, 46B in their expanded conditions are sized so to define a bracketed region 82 therebetween. Bracketed region 82 is preferably sized to completely contain the tissue mass including target tissue 44. When so bracketed, the health professional can locate target tissue 44 by virtue of the expanded mesh devices 46. In one embodiment mesh devices 46A, 46B are harder than the surrounding tissue so that target tissue 44 within bracketed region 82 may be found by palpation. In addition, expanded meshed devices 46A, 46B guide a surgeon in locating and excising the entire target mass using surgical techniques. The using of bracketing guides 46A, 46B is important because target tissue 44 is often difficult to differentiate from surrounding tissue both in appearance and in feel. After the surgeon has accessed target tissue 44, guided by bracketing mesh devices 46, the entire suspect tissue mass 84 can be removed as a single mass as suggested in FIG. 5D. It is expected that the device of FIGS. 5A–5D may be useful in both percutaneous and open incisional situations.

Figure 6A:
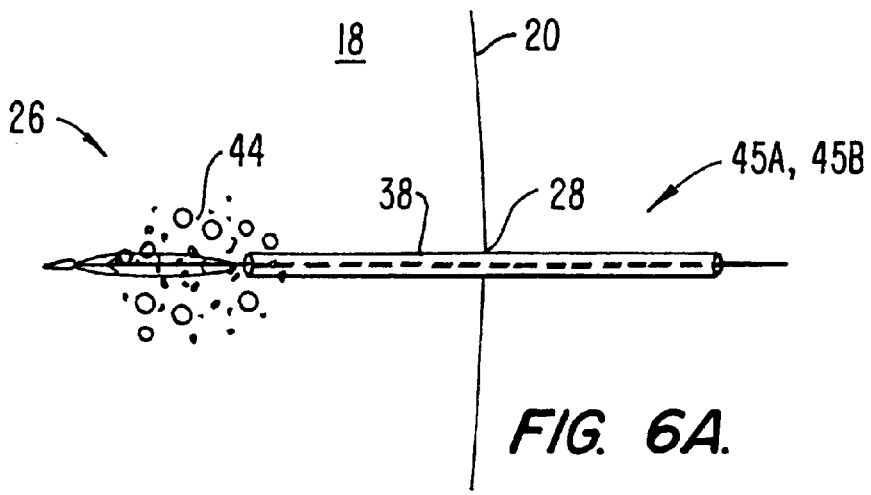
FIGS. 6A–6C show the use of a pair of locational elements, one of which is left in place after target tissue is removed to provide guidance for re-access to the target site.
Figure 6B:
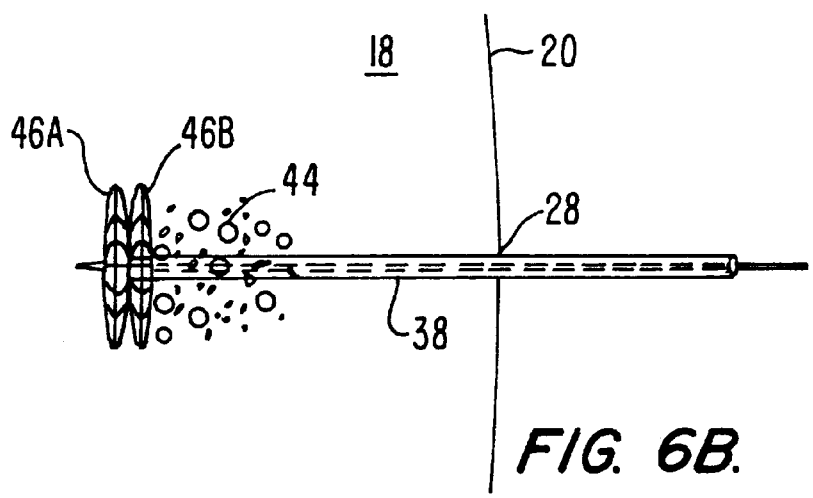
Figure 6C:
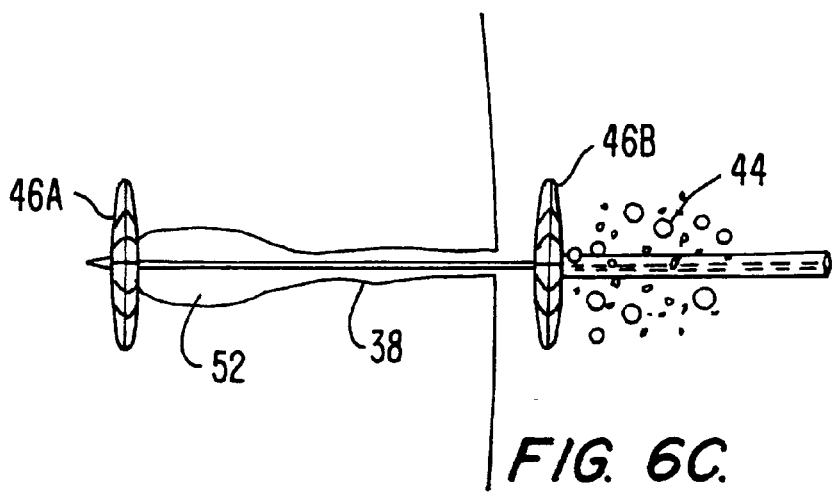

FIG. 6A–6C show the use of essentially the same type of structure as in FIGS. 5A–5D but for a different purpose. In this case devices 45 are used as locational elements. In the preferred embodiment both of the locational elements have radially expandable elements, such as mesh devices 46, both of which are positioned distally of target tissue 44. After removal of target tissue 44, which may occur along with proximal device 45B, device 45A remains in place adjacent to the excisional site or void 52 created by the removal of target tissue 44. This may be used to help maintain void 52 open to aid re-access to the site. Maintaining void 52 open also permits insertion of a space-saving device or structure into void 52. Instead of using two radially expandable elements as portions of the locational devices, locational device 45A could be simply, for example, a catheter shaft in which with the distal end would remain at the distal end of excisional site 52.

Modification and variation can be made to the disclosed embodiments without departing from the subject of the invention as defined in the following claims. For example, collapsing mesh device 46 could be replaced by, for example, an expandable balloon or an expandable malecot.

Any and all patents, patents applications and printed publications referred to above are hereby incorporated by reference.

What is claimed is:

1. A method for removing target material from a target site within a patient, comprising:

percutaneously placing an expandable blocking element along a tissue tract, the tissue tract connecting the target site and an access site in the patient's skin, at a first position distal of the target material;

expanding the expandable blocking element;

percutaneously placing a removing element along the tissue tract at a second position;

at least substantially surrounding the target material with the blocking element and the removing element; and percutaneously removing the blocking element, the removing element and the target material therewith from the patient along the tissue tract.

2. The method according to claim 1 wherein the first percutaneously placing step is carried out using a radially expandable, tubular mesh material as the expandable blocking element.

3. The method according to claim 1 wherein the second percutaneously placing step is carried out using a tubular mesh element having a radially expandable, open distal end.

4. The method according to claim 1 wherein the target material is at least substantially completely surrounded by the blocking element and the removing element following the surrounding step.

5. The method according to claim 1 further comprising at least partially radially collapsing the removing element prior to the removing step and maintaining the removing element in an at least partially radially collapsed condition during the removing step.

6. The method according to claim 5 further comprising at least partly radially collapsing the blocking element prior to the removing step.

* * * * *